United States Patent
Agricola et al.

(10) Patent No.: US 10,492,701 B2
(45) Date of Patent: Dec. 3, 2019

(54) FLEXIBLE CONDUCTIVE TRACK ARRANGEMENT AND MANUFACTURING METHOD

(71) Applicant: KONINKLIJKE PHILIPS N.V., Eindhoven (NL)

(72) Inventors: Franciscus Theodorus Agricola, Waalre (NL); Alfons Wouter Groenland, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 194 days.

(21) Appl. No.: 15/027,314

(22) PCT Filed: Sep. 29, 2014

(86) PCT No.: PCT/EP2014/070795
§ 371 (c)(1),
(2) Date: Apr. 5, 2016

(87) PCT Pub. No.: WO2015/052029
PCT Pub. Date: Apr. 16, 2015

(65) Prior Publication Data
US 2016/0249822 A1    Sep. 1, 2016

(30) Foreign Application Priority Data
Oct. 7, 2013    (EP) .................................... 13187478

(51) Int. Cl.
*B21D 13/00*        (2006.01)
*A61B 5/04*         (2006.01)
(Continued)

(52) U.S. Cl.
CPC ........ *A61B 5/04001* (2013.01); *A61N 1/0541* (2013.01); *A61N 1/36036* (2017.08);
(Continued)

(58) Field of Classification Search
None
See application file for complete search history.

(56) References Cited

U.S. PATENT DOCUMENTS

| 5,358,514 A | 10/1994 | Schulman |
| 8,224,435 B2 | 7/2012 | Gyory |

(Continued)

FOREIGN PATENT DOCUMENTS

| CN | 103167729 A | 6/2013 |
| RU | 2421253 C1 | 4/2011 |

(Continued)

OTHER PUBLICATIONS

"Definition of Corrugate", Merriam-Webster, https://www.merriam-webster.com/dictionary/corrugate, accessed Apr. 3, 2018.*

(Continued)

*Primary Examiner* — Seth Dumbris

(57) ABSTRACT

A flexible conductive track arrangement has a pre-flexing condition in which the arrangement is generally planar. Conductive tracks are formed from a metal layer and they are covered above and below by insulator layers. The elongate conductive tracks are generally planar but locally corrugated perpendicularly to the general plane. This enables improved binding performance, for example to form tight windings using the conductive tracks.

11 Claims, 6 Drawing Sheets

(51) Int. Cl.
*A61N 1/05* (2006.01)
*H05K 1/02* (2006.01)
*H05K 3/00* (2006.01)
*A61N 1/36* (2006.01)
*H05K 1/03* (2006.01)
*H05K 3/28* (2006.01)

(52) U.S. Cl.
CPC ........... *H05K 1/028* (2013.01); *H05K 1/0298* (2013.01); *H05K 3/007* (2013.01); *H05K 1/036* (2013.01); *H05K 1/0393* (2013.01); *H05K 3/0058* (2013.01); *H05K 3/28* (2013.01); *H05K 2201/051* (2013.01); *H05K 2201/09281* (2013.01); *H05K 2201/10151* (2013.01); *H05K 2203/0384* (2013.01); *H05K 2203/0769* (2013.01); *H05K 2203/1322* (2013.01); *H05K 2203/308* (2013.01); *Y10T 428/1241* (2015.01); *Y10T 428/12417* (2015.01)

(56) References Cited

U.S. PATENT DOCUMENTS

| | | | |
|---|---|---|---|
| 2004/0147992 A1* | 7/2004 | Bluger | A61N 1/0541 607/116 |
| 2007/0219551 A1 | 9/2007 | Honour | |
| 2009/0026462 A1 | 1/2009 | Hashiguchi | |
| 2009/0054960 A1* | 2/2009 | Stolen | A61B 18/1492 607/116 |
| 2011/0098719 A1 | 4/2011 | Llinas | |
| 2011/0224766 A1* | 9/2011 | Tol | A61N 1/0534 607/116 |
| 2012/0277835 A1 | 11/2012 | Della Santina | |
| 2012/0310258 A1* | 12/2012 | Llinas | A61N 1/0541 606/130 |

FOREIGN PATENT DOCUMENTS

| | | | | |
|---|---|---|---|---|
| WO | WO9936193 A1 | | 7/1999 | |
| WO | WO03041092 | * | 5/2003 | ............... H01B 5/14 |
| WO | WO2008140376 | * | 11/2008 | ............... A61N 1/05 |

OTHER PUBLICATIONS

Rosset S. et al., "Flexible and Stretchable Electrodes for Dielectric Elastomer Actuators", Applied Physics A, Feb. 2013, vol. 110, Issue 2, pp. 281-307.

Wang K. et al., "Towards Circuit Integration on Fully Flexible Parylene Substrates", Engineering in Medicine and Biology Society, 31st Annual International Conference of the IEEE EMBS, vol. 2009, pp. 5866-5869, Sep. 2-6, 2009.

* cited by examiner

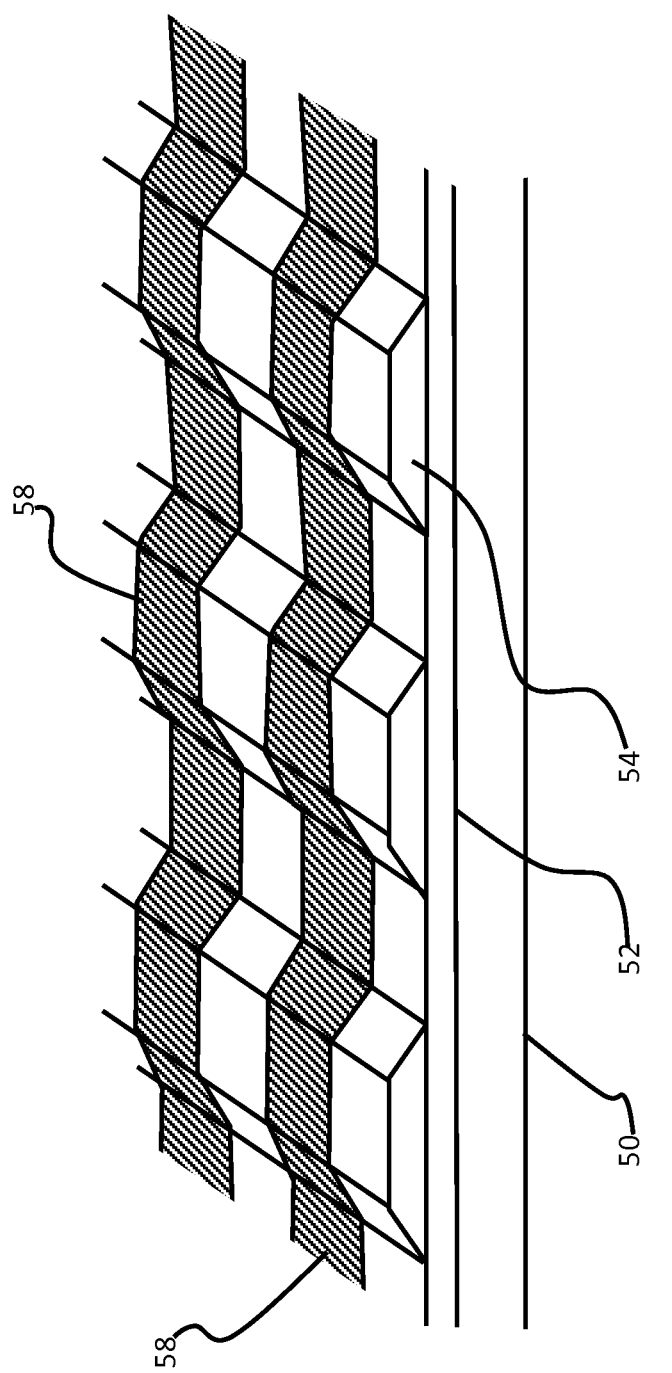

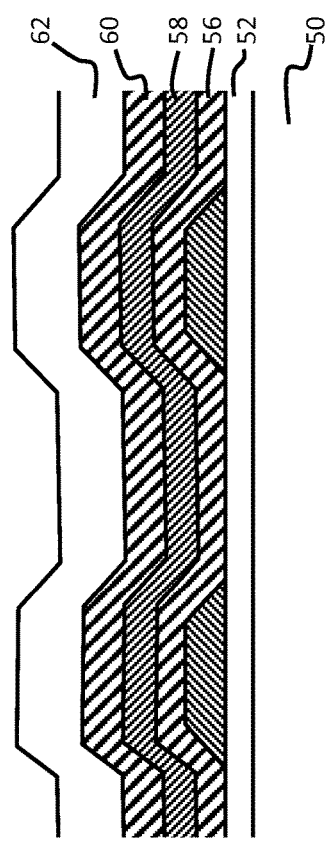
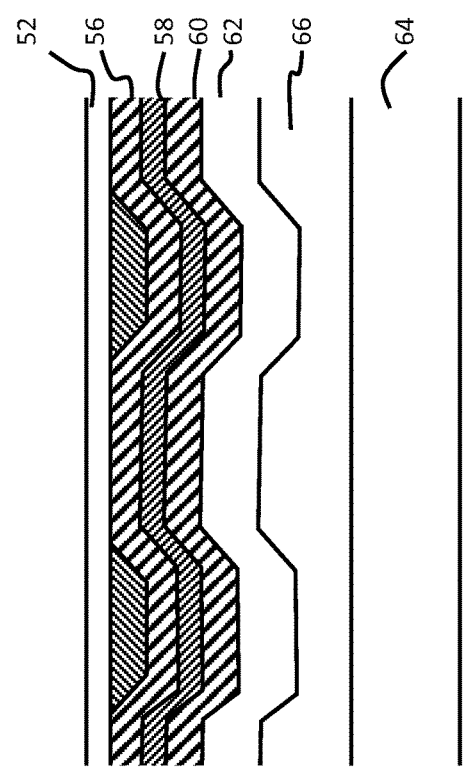
FIG. 7a
FIG. 7b

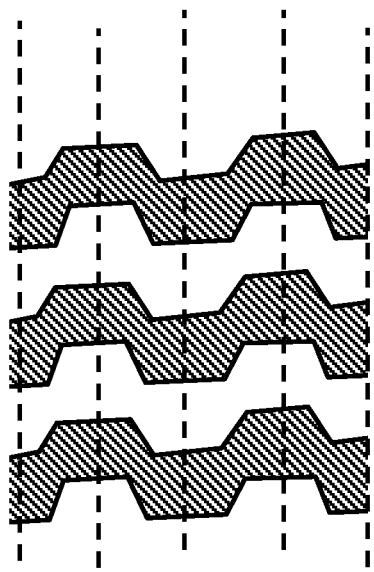
FIG. 9
FIG. 8

FLEXIBLE CONDUCTIVE TRACK ARRANGEMENT AND MANUFACTURING METHOD

FIELD OF THE INVENTION

This invention relates to a conductive track arrangement for conducting signals or power between remote locations, and which is flexible so that it can be deformed into a desired shape. This deformation is for example desired so that the tracks can be tightly wound around a carrier so that they occupy a minimum amount of space.

The invention also relates to a conductor arrangement comprising the conductive track arrangement wound around a carrier.

The invention also relates to an implantable device for stimulation or sensing of neurons.

The invention further relates to a method of forming the conductive track and the conductor arrangement.

BACKGROUND OF THE INVENTION

Winding of conductive tracks tightly around a carrier is often used in medical devices that can be used for stimulation and/or detection of neuron signals in the body (human and/or animal) by inserting them temporarily or permanently (implantable) in the body. The conductive tracks are for example required to relay signals between a sensor and/or stimulation device within the body and processing units and circuitry outside the body. The insertable/implantable part of the device needs to have certain dimensions that are usually rather small. The dimensions depend on the particular implementation. Specific known examples of such implementations are cochlea implants, but others such as (deep) brain stimulation devices, or muscle stimulation devices can be conceived. The current invention can be used for all such devices.

For example, the cochlea of the human ear contains hair cells that are essential to the perception of sound. Sound vibrations distort certain structures of the cochlea which in turn distort the hair cells. This initiates electrical impulses in the hair cells which are conveyed to the fibers of the auditory nerve and ultimately to the brain.

Some instances of human hearing loss are attributed to extensive destruction of the hair cells. When this occurs, though the structures of the cochlea may otherwise be substantially intact, and the auditory nerve may be partially or completely intact, the auditory response is significantly impaired or non-existent.

Cochlea implants directly stimulate the auditory nerves inside the inner ear. In a traditional cochlear implant system, a microphone acquires sound from the environment. The sound is then selectively filtered by a speech processor, using various filter bank strategies such as Fast Fourier Transforms, to divide the signal into different frequency bands. Once processed, the signal is then sent to a transmitter, a coil held in position by a magnet placed behind the external ear. This transmitter sends the processed signal to the internal device by electromagnetic induction.

Embedded in the skull, behind the ear is a receiver which converts the signal into electric impulses and sends them through an internal cable to electrodes. Conventional cochlear implants are made of multiple platinum electrodes or similar conductive material, connected to platinum wire and embedded in a silicone body. These electrodes then act to stimulate the auditory nerve fibers by generating an electric field when the electrical current is routed to them.

It is known that the cochlea implant should have a small insertion area so that the installation of the cochlear implant does not damage cochlear structures. Although perhaps not always necessary, implants for (deep) brain stimulation or other purposes are also likely to benefit from the smaller insertion area. This puts constraints on the cable dimensions of an insertable device and especially for the cochlea device.

One known design is based on a long strip of electrodes, which are then wound around a carrier to form a spiral strip cochlea implant. This provides the desired tubular shape for insertion into the cochlea. An example of this type of arrangement is for example disclosed in US 2012/0310258. The electrode design includes conductive and dielectric layers, to provide isolation of different electrode lines. The electrode design provides a limit to how tightly the strip can be wound, and this in turn provides a limit to how small the tube can be made and thus to the insertion area. In particular, bending the strip with a bend radius which is too small can result in damage of one or more of the layers forming the structure. Hence there is a need for an improved insertable/implantable device with a smaller insertion area

SUMMARY OF THE INVENTION

It is an object of the invention to provide an improved insertable/implantable device with respect to the aforementioned problem.

The problem is solved by the invention as defined by the independent claims. The dependent claims provide advantageous embodiments.

By providing corrugations perpendicular to the general plane of the tracks, the bending performance of the arrangement is improved, so that tighter bends can be formed than without the corrugations. The pre-flexing condition is an unstressed configuration in which the arrangement can be conveniently manufactured without having to put it in a difficult (wound) condition. Thus, the corrugated structure is not formed after manufacture which would cause stresses in the structure, but is instead part of the manufactured design.

The corrugations can have a height in the range of 0.5 to 10 μm, more preferably 1 to 2 μm and they can have a pitch in the range of 5 to 50 μm, more preferably 5 to 10 μm. The structure can be formed based on thin films. Part of the films can be made of organic/polymeric materials such as plastics.

The conductive tracks may be elongated. Lengths can vary from 1 cm to as long as desired. Typical length ranges extend between 5 and 40 cm, between 10 and 40 cm, or between 20 and 30 cm. The set of conductive tracks can comprise 10 to 30 tracks (e.g. 16 tracks), with an overall width of 0.2 to 1.0 mm (e.g. 0.6 mm). The wires may for example be 17 μm wide, with a 17 μm gap.

The first and second insulator layers can each comprise a ceramic sub-layer adjacent the metal layer and an outer polymer sub-layer. Thus, multiple layers can be used to provide the desired insulation properties as well as to provide an ion barrier. For example, a lower ceramic layer can comprise a 500 nm LPCVD ceramic layer, the metal layer can comprise a 2 μm gold layer encapsulated on both sides by 250 nm platinum and a top 500 nm PECVD ceramic layer. The ceramic can by SiN/TEOS. The structure can be encapsulated in parylene (for example 5 μm) that, if needed, is partly opened up for electrode exposure. A conductor arrangement including the flexible conductive track arrangement can have a smaller insertion area, because of tighter winding of the conductive track arrangement enabled by the corrugations in it. Thus, one or more of the cross sectional dimension of the carrier (e.g. the diameter if it is of tubular shape) may be smaller than 1 mm or, as preferred for cochlea devices smaller than 0.5 mm. The carrier can have a number of shapes according to desire. Example shapes include tubular or cylindrical with rectangular, oval or circular crosssection or even other crosssections. Preferably the crosssection is oval or circular. The carrier may have a smaller crosssection at one location than on another location. Hence it can be conical, or have sections of different but constant diameter wherein the smallest dimension can be smaller than 1 mm or even smaller than 0.5 mm. Alternatively, the carrier can be bar shaped with somewhat rounded edges extending in the bar extension direction.

The flexible conductive track arrangement can be wound around the carrier in different ways. It may be wound with the tracks extending perpendicular to the direction in which the carrier extends. Preferably, however it is wound spirally around the carrier (see Figs).

The advantages described above enable an insertable or implantable device comprising the conductor track that can be used in the cochlea area. Without loss of advantages effect based on smaller insertion area and/or device reliability, such device can also be used in other areas such as for example (deep) brain stimulation or muscle nerve stimulation.

The method of the invention provides a corrugated structure at manufacture, rather than by deformation. The removal of the adhesion layer may be done using physical methods such as heating if it is a thermal release layer. Preferably the adhesion layer is dissolvable in a solvent and the removal of it is done by dissolution in the solvent. The stepped layer can comprise a series of ridges, for example with a height in the range of 0.5 to 10 μm, more preferably 1 to 2 μm, and a pitch in the range of 5 to 50 μm, more preferably 5 to 10 μm.

BRIEF DESCRIPTION OF THE DRAWINGS

Examples of the invention will now be described in detail with reference to the accompanying drawings, in which:

FIG. 6 is used to show the shape of the tracks of the track arrangement of the invention in perspective view and corresponds to the structure at the end of the steps of FIG. 5;

FIG. 8 shows a first example of the tracks of the invention in plan view; and

FIG. 9 shows a second example of the tracks of the invention in plan view.

DETAILED DESCRIPTION OF THE EMBODIMENTS

The invention provides a flexible conductive track arrangement having a pre-flexing condition in which the arrangement is generally planar. Conductive tracks are formed from a metal layer and they are covered above and below by insulator layers. The elongate conductive tracks are generally planar but locally corrugated perpendicularly to the general plane. This enables improved binding performance, for example to form tight windings using the conductive tracks.

Figure 1:
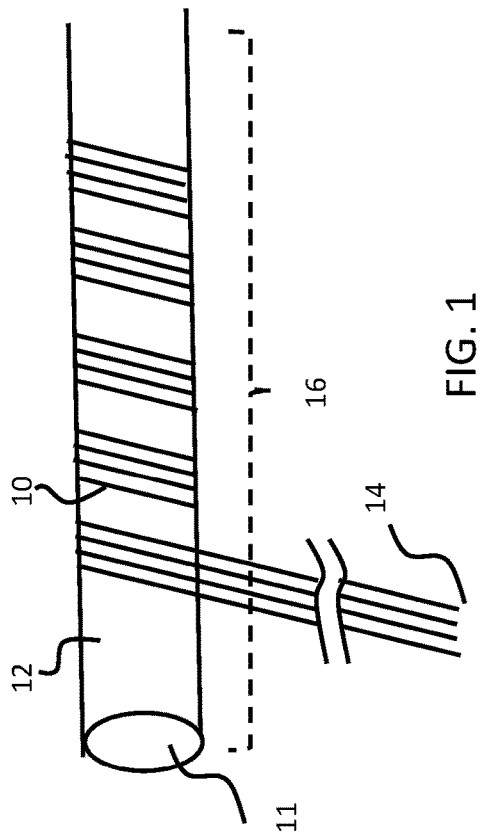
FIG. 1 shows a conductive track arrangement wound in a spiral around a tubular support, for example as can be used in cochlea implants.

FIG. 1 shows a conductive track arrangement 10 wound in a spiral around a tubular support 12 having a tubular section 16 with a crosssection 11, for example as can be used in cochlea implants and in deep brain stimulation implants. The tracks terminate at an electrode arrangement 14 for implantation into the cochlea, and the opposite end of the track arrangement couples to a transmitter for sending signals to the electrode arrangement. The transmitter can for example be mounted internally of the patient, in wireless inductive communication with an earpiece worn by the user, which generates the required signals in response a microphone input.

Figure 2:
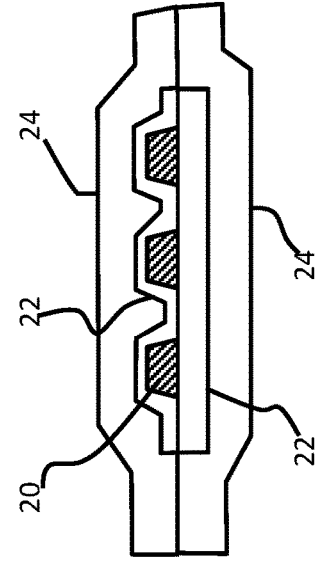
FIG. 2 shows a cross section of the known track arrangement across its length.

FIG. 2 shows a cross section of the known track arrangement across its length. The tracks are formed as flat metal tracks 20 for example of gold or platinum, coated above and below with an insulator, such as a ceramic layer 22 (for example silicon nitride or silicon oxide) and a polymer protection layer 24 such as parylene or polyimide.

Figure 3:
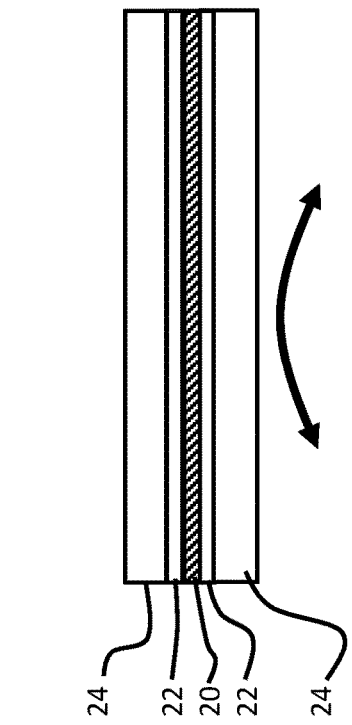
FIG. 3 shows a cross section of the known track arrangement along its length.

FIG. 3 shows a cross section of the known track arrangement along its length, and shows that the track is flat along its length.

This arrangement can be damaged if it is bent too sharply. The bending takes place in the direction shown by the arrow in FIG. 3 when performing the winding shown in FIG. 1. The radius of curvature which can be applied is limited by the physical and mechanical properties of the layers.

Figure 4:
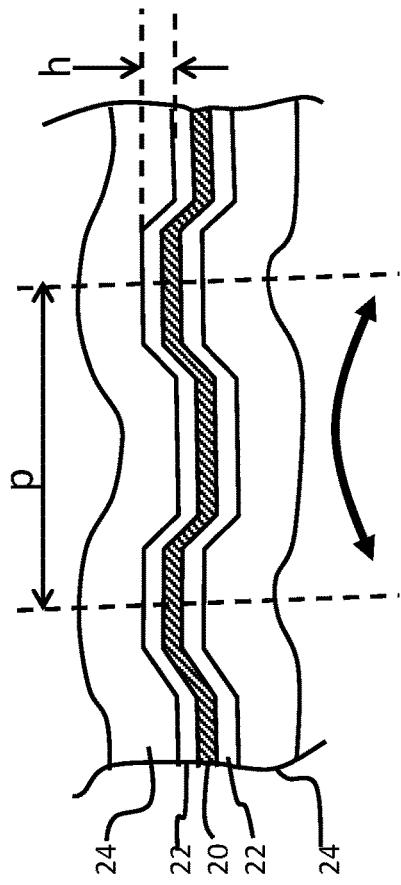
FIG. 4 shows a cross section of a track arrangement of the invention along its length.

FIG. 4 shows a cross section of a track arrangement of the invention along its length.

The arrangement is again generally planar, and has the same insulating and protective layers above and below the tracks. The tracks are however locally corrugated perpendicularly to the general plane of the arrangement.

The corrugations provide height variation along the length of the tracks, and this enables higher bending forces to be withstood. As a result a smaller bending radius can be used.

The device is manufactured with the corrugated shape, rather than being deformed into the shape after manufacture in a flat configuration. This means the corrugated shape is for an unstressed configuration. This also means that manufacture is simpler (in planar state) than when in wound state.

The corrugations for example can have a height in the range of 0.5 to 10 μm, more preferably 1 to 2 μm. This height is shown as h in FIG. 4, and is for example the change in height from the top a given layer at the bottom of the corrugation to the top of that layer at the top of the corrugation. The corrugations have a pitch in the range of 5 to 50 μm, more preferably 5 to 10 μm. This is shown as p in FIG. 4.

The overall length can for example be in the range 20 cm to 30 cm. A single film can contain 16 wires for example 17 μm wide, with a 17 μm gap. The overall film can typically be 0.6 mm wide.

The conductive track arrangement of the invention can be manufactured by modifying a known manufacturing method for flexible conductors, by providing a contoured initial substrate over which the various layers are deposited.

By way of example, the article "Towards Circuit Integration on Fully Flexible Parylene Substrates" presented in the 31st Annual International Conference of the IEEE EMBS, Minneapolis, USA, Sep. 2-6, 2009 of Ke Wang et. al. discloses a method for manufacturing a microelectrode structure in which a metal electrode layer has oxide layers above and below and a parylene layer above and below the oxide layers. Two opposing sacrificial substrates are used in the process. The disclosed method modified as described below can be used to manufacture the device of the invention. It is therefore incorporated in its entirety.

Figure 5A:
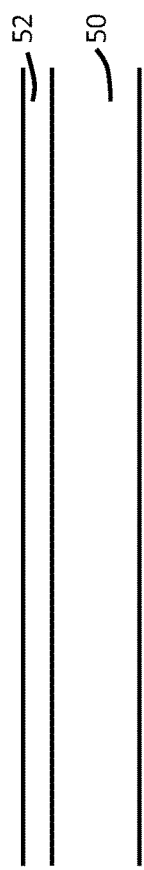
FIG. 5 shows first manufacturing steps of one example of method in accordance with the invention.
Figure 5B:
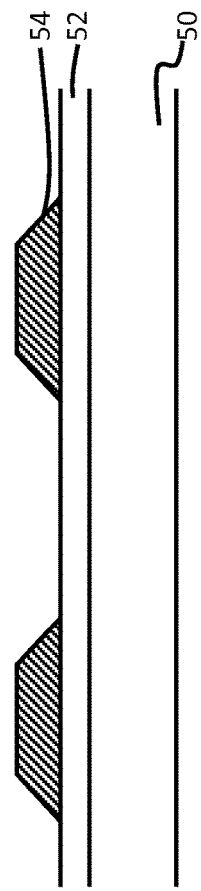

FIG. 5 shows a first sub-set of the manufacturing steps of one example of method in accordance with the invention, which can be considered to be a modification to the process disclosed in the Ke Wang et. al. article referenced above, in particular by providing the stepped support layer described below with reference to FIG. 5b.

FIG. 5a shows a substrate 50 such as a silicon wafer, over which an etch stop layer 52 is provided, such as silicon nitride deposited by LPCVD.

FIG. 5b shows a stepped layer 54 provided over the etch stop layer 52. This can be a metal layer such as aluminium, but other materials can be used. As will be seen below, this layer is etched away later on, so it is selected to match the etch processes used.

In the example shown, the layer 54 comprises separate islands which provide raised ridges. In one example, the ridges have a height in the range of 0.5 to 10 µm, more preferably 1 to 2 µm, and the ridges have a pitch in the range of 5 to 50 µm, more preferably 5 to 10 µm. The ridges define a corrugation in a subsequently deposited conductor layer.

It can be seen in FIG. 5b that the islands have sloped edges. Aluminum can be etched in a wet chemical etching process (PES etchant) when the masking photoresist is prepared. Alternatively, the metal thin film can be etched in an ion beam etcher, where the angle is defined by the angle of maximum sputter yield (which is a material property).

Figure 5C:
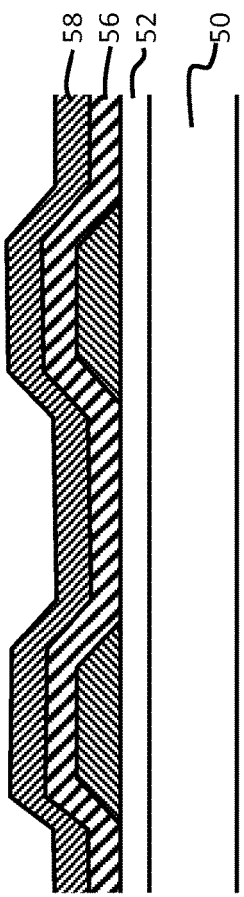

As shown in FIG. 5c, a first insulator layer 56 is formed above the stepped layer comprising a ceramic layer such as silicon oxide or silicon nitride or an oxide nitride oxide stack. A metal layer 58 is formed over the first insulator layer 56 and is patterned to form elongate conductive tracks. The metal can be platinum.

FIG. 6 shows the construction at this point of the process, in perspective view, in order to show more clearly the shape of the patterned conductor tracks. The insulator layer 56 is omitted for improved clarity. As shown, the elongate conductive tracks 58 are generally planar but locally corrugated perpendicularly to the general plane with a shape corresponding to the stepped layer.

FIG. 7 shows the proceeding manufacturing steps.

FIG. 7a shows the addition of a second insulator layer 60 over the metal layer (again a ceramic oxide or nitride or stack of layers) followed by a polymer insulating protection layer 62 such a parylene. The insulator layers 60,62 can be considered as sub-layers of an overall insulator arrangement. The insulator arrangement can comprise one or other or both of these types of layer (i.e. ceramic and/or polymer layers).

The structure at this stage is bonded to a second substrate 64 using a dissolvable adhesive 66, on the opposite side to the first substrate 20. FIG. 7b shows the structure inverted since the second substrate 64 then provides the support. The first substrate 50 is then removed by etching down to the etch stop layer 52.

Figure 7C:
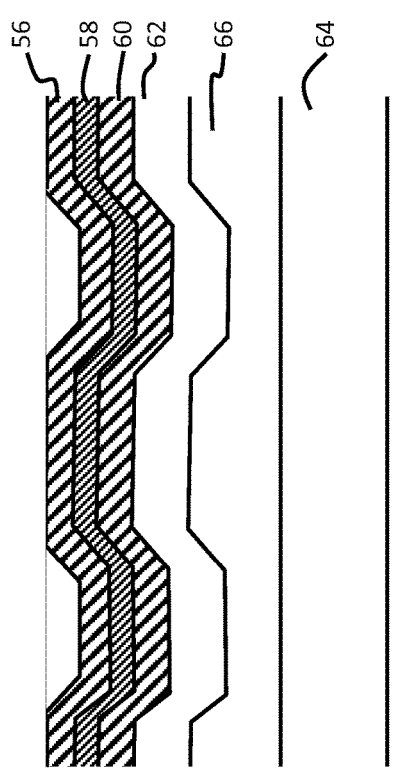
FIG. 7 shows further manufacturing steps of the example of method in accordance with the invention.

As shown in FIG. 7c, the etch stop layer and the stepped layer are then etched away. Optionally, the etch stop layer can be patterned if parts are desired to remain. A wet Al etch can for example be used. A second polymer layer 70 is then deposited over the second insulator layer 56. Again, the two layers 56,70 can be considered as sub-layers of an overall insulator arrangement, which may have one or both of the polymer and ceramic insulator sub-layers.

Figure 7D:
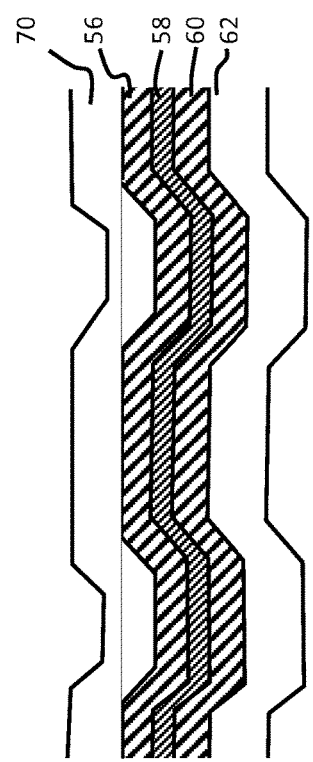

The adhesive 66 is then dissolved to remove the second substrate 64 giving the completed product as shown in FIG. 7d.

The conductive tracks meander in height but are completely covered by the insulating arrangement to provide electrical separation between tracks as well as enabling overlapping of the tracks when wound. This enables a reduced bending radius and improved robustness. The structure can handle increased twist and elongation forces.

The conductive tracks can be straight, as shown in plan view in FIG. 8. However, they may also meander in the general plane, as shown in FIG. 9, where the dotted lines represent the steps in the perpendicular corrugations. This structure effectively has corrugations in two orthogonal planes. This improves the bending behavior in the orthogonal direction, so that for example the bending performance of the wound tubular device is improved.

The invention can be applied to deep brain implants and cochlea implants, as explained above. However, the invention more generally enables an electrode arrangement to be deformed into a desired shape, which may include some tight bends and other less tight bends. The invention is of general interest for devices that are insertable or implantable in humans or animals, and for neurostimulation applications generally, where there is generally a desire for miniaturization. Another example is spinal implants.

As an example, the conductive track arrangement can be used in a cochlea device as described in US 2012/0310258 which is incorporated in its entirety in the current description. The arrangement is then wound around the carrier as described. A device according to the invention can have more than one section 16 each having a different cross section (see FIG. 1 for the meaning of cross section and section). Auxiliary functions (signal source, processor sensors etc.) can be added to complete the device. Other implantable or insertable devices can be made in similar ways without difficulty by incorporating the functionality needed to the conductor track arrangement.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A flexible conductive track arrangement, comprising:
a set of conductive tracks formed from a metal layer;
a first insulator layer above the conductive tracks; and
a second insulator layer below the conductive tracks,
wherein the conductive tracks extend in a plane and are locally corrugated perpendicular to the plane, the set of conductive tracks being wound around a carrier, and
wherein the corrugations are formed by two sloped sides connected to a top surface that is parallel to a bottom surface creating separate islands with raised ridges.

2. The flexible conductive track arrangement according to claim 1, wherein the corrugations have a height in the range of 0.5 to 10 µm.

3. The flexible conductive track arrangement according to claim 1, wherein the corrugations have a pitch in the range of 5 to 50 µm.

4. The flexible conductive track arrangement according to claim 1, wherein the conductive track length is in the range of 10 cm to 40 cm.

5. The flexible conductive track arrangement according to claim 1, wherein the set of conductive tracks comprises 10 to 30 tracks.

6. The flexible conductive track arrangement according to claim 1, wherein the set of tracks has an overall width between 0.2 and 1.0 mm.

7. The flexible conductive track arrangement according to claim 1, wherein the first and second insulator layers each comprise a ceramic sub-layer adjacent the metal layer and an outer polymer sub-layer.

8. A conductor arrangement, comprising:
a carrier; and
a flexible conductive track arrangement comprising a set of conductive tracks formed from a metal layer, a first insulator layer above the conductive tracks, and a second insulator layer below the conductive tracks, wherein the conductive tracks extend in a plane and are locally corrugated perpendicular to the plane, the flexible conductive track arrangement being wound around the carrier, and wherein the corrugations are formed by two sloped sides connected to a top surface that is parallel to a bottom surface creating separate islands with raised ridges.

9. The conductor arrangement according to claim 8, wherein the carrier comprises a section having a tubular or cylindrical shape.

10. The conductor arrangement according to claim 9, wherein in at least one location within the section the carrier comprises a cross section with a cross sectional dimension of less than 1 mm or less than 0.5 mm.

11. The conductor arrangement according to claim 10, wherein the cross section is circular and the cross sectional dimension is the diameter.

* * * * *